United States Patent
Gupta et al.

(10) Patent No.: US 10,710,982 B2
(45) Date of Patent: Jul. 14, 2020

(54) (S)-N-(3-6-ISOPROPOXYPYRIDIN-3-3YL)-1H-INDAZOL-5-YL)-1-(2-(4-4(1-METHYL-1H-1,2,4-TRIAZOL-3-YL)PHENYL)-3,6-DIHYDROPYRIDIN-1(2H-YL)-2-OXOETHYL)-3(METHYLTHIO)PYRROLIDINE-3-CARBOXAMIDE COMPOSITIONS FOR PHARMACEUTICAL PREPARATIONS

(71) Applicant: Merck Sharp & Dohme Corp., Rahway, NJ (US)

(72) Inventors: Pranav Gupta, Basking Ridge, NJ (US); Jiansheng Wan, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/789,123

(22) Filed: Feb. 12, 2020

(65) Prior Publication Data

US 2020/0181119 A1   Jun. 11, 2020

Related U.S. Application Data

(62) Division of application No. 15/536,496, filed as application No. PCT/US2015/065428 on Dec. 14, 2015, now Pat. No. 10,577,348.

(60) Provisional application No. 62/093,607, filed on Dec. 18, 2014.

(51) Int. Cl.
 *C07D 401/14* (2006.01)
 *A61K 31/444* (2006.01)
 *A61K 9/48* (2006.01)

(52) U.S. Cl.
 CPC .......... *C07D 401/14* (2013.01); *A61K 9/4833* (2013.01); *A61K 9/4866* (2013.01); *A61K 31/444* (2013.01)

(58) Field of Classification Search
 CPC .................................................. C07D 401/14
 USPC ....................................................... 546/256
 See application file for complete search history.

(56) References Cited

U.S. PATENT DOCUMENTS

2006/0160807 A1   7/2006   Aronov et al.
2009/0054397 A1   2/2009   Ohi et al.
2011/0189192 A1   8/2011   Cooper et al.
2011/0288102 A1   11/2011  Samatar
2013/0158020 A1   6/2013   Deng et al.
2014/0357681 A1   12/2014  Warashina et al.

FOREIGN PATENT DOCUMENTS

| EP | 2810660 B1 | 7/2017 |
| RU | 2454220 C2 | 6/2012 |
| WO | 2008021347 A2 | 2/2008 |
| WO | 2009105500 A1 | 8/2009 |
| WO | 2014196519 A1 | 12/2014 |

OTHER PUBLICATIONS

Bee, Timothy, Using Polymer Technology to Enhance Bioavailability, Pharm Tech Japan, 2011, 57-63, vol. 27, No. 10.
Bernstein, Joel, Polymorphism in Molecular Crystals, Polymorphism in Molecular Crystals, 2002, 115-118, 272.
Braga, D. et al, Making crystals from crystals: a green route to crystal engineering and polymorphism, The Royal Spciety of Chemistry, Jun. 15, 2005, 3635-3645.
Friesen, et al., Hydroxypropyl Methylcellulose Acetate Succinate-Based Spray-Dried Dispersions: An Overview, Molecular Pharmaceutics, 2008, 1003-1019, vol. 5. No. 6.
Ivanisevic, I. et al., Uses of X-Ray Powder Diffraction in the Pharmaceutical Industry, Pharmaceutical Sciences Encyclopedia: Drug Discovery, Development, and Manufacturing, 2010, p. 1-42.
Obara, S et al, Properties and Applications of Hypromellose Acetate Succinate (HPMCAS) for Solubility Enhancement Using Melt Extrusion, Melt Extrusion, 2013, 107-121.
Tanno, F et al., Evaluation of Hypromellose Acetate Succinate (HPMCAS) as a Carrier in Solid Dispersions, Drug Development and Industrial Pharmacy, 2004, pp. 9-17, 30-1.
Tanno, Fumie K., HPMCAS—in vitro, Pharmacology, 2013, 214-222, vol. 73, No. 4.
Ulrich, J, Crystallization, Kirk-Othmer Encyclopedia of Chemical Technology, 2002, 95-147, 8.
Vippagunta, S.R. et al., Crystalline Solids, Advanced Drug Delivery Reviews, 2001, 3-26, 48.

*Primary Examiner* — Patricia L Morris
(74) *Attorney, Agent, or Firm* — Jeffrey P. Bergman; Catherine D. Fitch (57) ABSTRACT

A composition comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide and hypromellose acetate succinate for pharmaceutical preparations, especially capsule preparations.

3 Claims, 4 Drawing Sheets

(S)-N-(3-6-ISOPROPOXYPYRIDIN-3-3YL)-1H-INDAZOL-5-YL)-1-(2-(4-4(1-METHYL-1H-1,2,4-TRIAZOL-3-YL)PHENYL)-3,6-DIHYDROPYRIDIN-1(2H-YL)-2-OXOETHYL)-3(METHYLTHIO)PYRROLIDINE-3-CARBOXAMIDE COMPOSITIONS FOR PHARMACEUTICAL PREPARATIONS

CROSS-REFERENCE TO RELATED APPLICATIONS

This application is a divisional of pending U.S. Ser. No. 15/536,496, filed Jun. 15, 2017 which is a the National Stage application of PCT/US2015/065428, filed Dec. 14, 2015, which claims the benefit of U.S. Provisional Application Ser. No. 62/093,607, filed Dec. 18, 2014, each of which is incorporated herein by reference in their entirety.

BACKGROUND OF THE INVENTION

WO2009/105500 describes ERK inhibitors, including procedures for making them and procedures for preparing pharmaceutical compositions comprising the ERK inhibitors.

Described pharmaceutical compositions include solid form preparations including powders, tablets, dispersible granules, capsules, cachets and suppositories for direct administration to a patient; liquid form preparations including solutions, suspensions and emulsions for direct administration to a patient; aerosol preparations suitable for inhalation; solid form preparations which are intended to be converted, shortly before use, to liquid form preparations, including solutions, suspensions and emulsions for subsequent administration to a patient; and transdermal compositions including creams, lotions, aerosols and/or emulsions for direct application to the patient or administration via transdermal patch.

(S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, a specific ERK inhibitor described in WO2009/105500, is most stable in crystalline hydrate Form 2. This form has poor solubility, and in order to efficiently prepare certain pharmaceutical compositions for administration to patients including tablet and capsules suitable for safe and effective oral administration, it is highly desirable to create amorphous dispersions to improve solubility wherein the amorphous form of the drug shall have higher apparent solubility compared to its crystalline counterparts.

The present invention provides a dispersion of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide having improved solubility which allows for efficient preparation of tablets and capsules suitable for safe and effective oral administration to a patient.

SUMMARY OF THE INVENTION

The invention is a composition comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide and hypromellose acetate succinate, methods for preparing the composition, and uses of the composition to prepare pharmaceutical preparations, including capsule preparations, for administration to a patient.

DETAILED DESCRIPTION OF THE INVENTION

The invention is a composition comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide and hypromellose acetate succinate.

In one embodiment, the composition comprises (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide and hypromellose acetate succinate, wherein the weight ratio of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide to hypromellose acetate succinate is between about 1:1 and 1:5. In another embodiment, the weight ratio is about 1:3.

The invention is also a film cast process for preparing a hard gelatin capsule comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide which comprises the steps of a) dissolving (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide free base hydrate form 2 and hypromellose acetate succinate in a solvent to form a solution, b) evaporating the solvent from the solution to form a film cast comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous form;

c) grinding the film cast to form a ground product.

The ground products can then be used to fill a hard gelatin capsule or a hydroxypropyl methylcellulose capsule or formulated into a tablet using conventional tableting procedures.

In an embodiment of the film cast process, the weight ratio of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide to hypromellose acetate succinate is between about 1:1 and 1:5. In another embodiment of the film cast process, the ratio is about 1:3. In another embodiment of the film cast process, the solvent is acetone.

The invention is also a hot melt extrusion process for preparing a hard gelatin capsule comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide which comprises the steps of a) blending (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide free base hydrate form 2 and hypromellose acetate succinate to form a blend, b) extruding the blend through a twin screw hot melt extruder to form an extrudate, c) quenching the extrudate on an air cooled conveyor belt or using a chilled roller to form quenched extrudate comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous form, d) pelletizing the extrudate to form pellets and subsequently milling the pellets to form a ground product.

The ground product can then be blended with a superdisintegrant which can then be filled into a hard gelatin capsule. Alternatively, the quenched extrudate can be pelletized, milled, sieved and then used to form a tablet using conventional tableting procedures.

In an embodiment of the hot melt extrusion process, the weight ratio of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide to hypromellose acetate succinate is between about 1:1 and 1:5. In another embodiment, the ratio is about 1:3.

Hypromellose acetate succinate used in the above processes can be in granular form or fine powder. Various grades are suitable including grade M which has a pH sensitivity of ≥6.0; grade L which has a pH sensitivity of ≥5.5, and grade H which has a pH sensitivity of ≥6.8. Superdisintegrant can be crospovidone.

The invention is also a compound form of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide selected from Free Base Hydrate Form 2, HCl Form 1, HCl Hydrate Form 1, and HCl Hydrate Form 2. In an embodiment of the invention the form is Free Base Hydrate Form 2. In an embodiment of the invention the form is HCl Form 1. In an embodiment of the invention the form is HCl Hydrate Form 1. In an embodiment of the invention the form is HCl Hydrate Form 2.

(S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, structure I below:

and method for its preparation, is described in patent publication WO2009/105500 (compound A6). (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide is also available from Active Biochem CAT # A-1191. The compound, which inhibits ERK activity (i.e., ERK1 and ERK2 activity), may be useful for treating a broad spectrum of cancers, such as, for example, melanoma, pancreatic cancer, thryroid cancer, colorectal cancer, lung cancer, breast cancer, and ovarian cancer.

Preparation:

(S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide free base synthesis is 19 steps. Compound preparation is divided into three intermediate preparations A, B and C followed by coupling of the intermediates. All intermediates start with commercially available compounds. Compound 5 is prepared by reaction of the commercially available bromo-4-cyanobenzene with methyl hydrazine under acidic conditions to form the hydrazinoimidate 2 in modest yield. After reaction with formic acid in two steps the bromophenyl-N-methyl triazole intermediate 3 is obtained. The tetrahydropyridine ring is introduced by a Suzuki reaction of the commercially available Boc protected tetrahydropyridine-boronate to obtain the tricyclic ring system 4. Chloroacetamide 5 is obtained in excellent yield by reaction of the deprotected 4 with chloroacetylchloride. The pyrrolidine core 10a is obtained in good yield in 5 steps starting from commercially available 6. Reaction with thionylchloride gave the thiomethyl olefin 7. Cycloaddition (2+3) gave 8 followed by removal of the benzyl protection group to give 9. L-Tartaric acid resolution of the pyrrolidine core gives the pure (S) enantiomer 9 after filtration from methanol. After protection as the Boc derivative and hydrolysis of the methyl ester, 10 is obtain in overall 50% yield. Compound 17 is obtained from commercially available indazole 11. Bromination at the 3-position of indazole 11 proceeded in excellent yield without chromatography to obtain 12. Suzuki reaction of the bromo compound 12 with 14 gave the nitro indazole 16 after chromatography. Reduction of 16 gave aniline 17 as an oil in quantitative yield without chromatography. The final coupling of the intermediates proceeded by coupling 17 with 10a to obtain 18 in good yield. After deprotection of the Boc and Trityl groups the final coupling with 5 gave (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3- carboxamide after chromatography. Final purification was carried out by crystallization from methanol/diethylether. This synthetic route has been conducted on a scale that delivered (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide free base (Compound I).

Synthesis from Key Intermediates 5, 10 and 17

Preparation A:

Preparation B:

Preparation C:

-continued

Final Coupling:

Compound I

Preparation of Free Base Hydrate Form 2

Compound I was suspended in neat water at ambient temperature. Mixture was aged for at least one day yielding a crystalline form (Free Base Hydrate Form 2).

Preparation of HCl Form 1

HCl Hydrate Form 1 or HCl Hydrate Form 2 was suspended in ethyl acetate, toluene, acetonitrile, isopropyl acetate, acetone or tetrahydrofuran (THF) at ambient temperature. Mixtures were aged for at least one day yielding a crystalline form (HCl Form 1).

Preparation of HCl Hydrate Form 1

Compound I was suspended in aqueous isopropanol mixtures followed by the addition of hydrochloric acid. Mixtures were aged at ambient temperature for at least one day yielding a crystalline salt (HCl Hydrate Form 1).

Preparation of HCl Hydrate Form 2

Compound I was suspended in aqueous acetone mixtures followed by the addition of hydrochloric acid. Mixtures were aged at ambient temperature for at least one day yielding a crystalline salt (HCl Hydrate Form 2).

HCl Form 1 was suspended in neat water at ambient temperature. Mixture was aged for at least one day yielding a crystalline form (HCl Hydrate Form 2).

Free Base Hydrate Form 2 Powder X-Ray Diffraction Data

Figure 1:
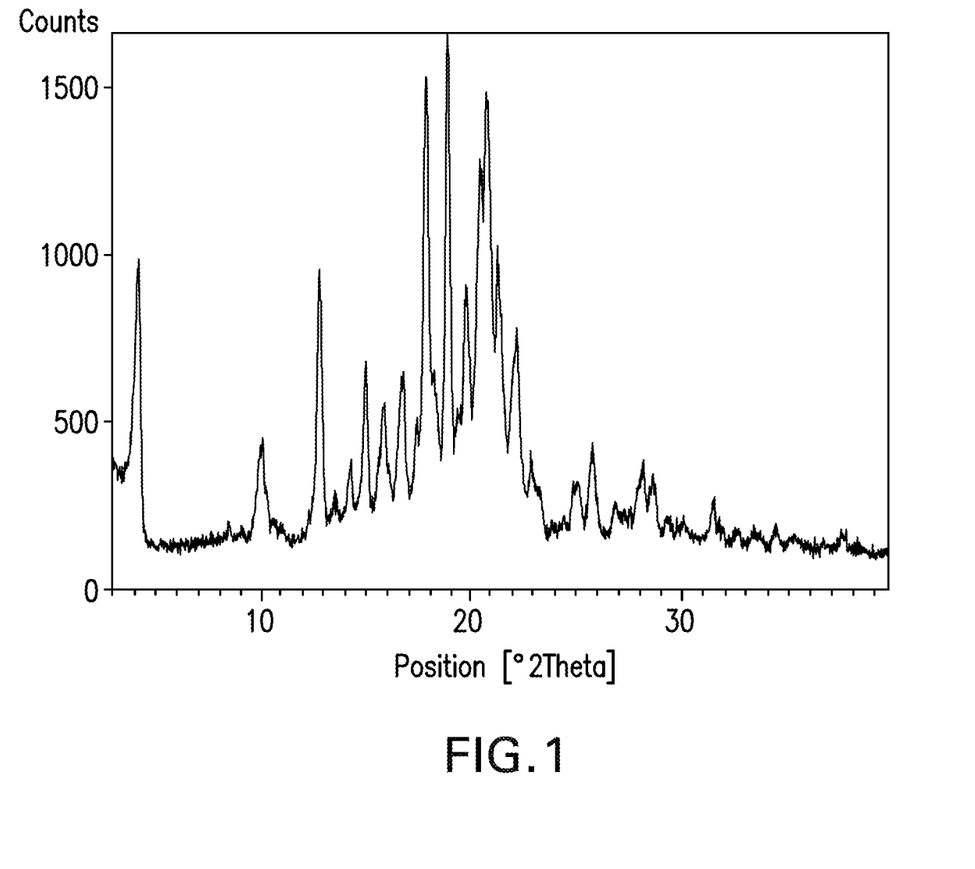
FIG. 1 is graph of Powder X-Ray Diffraction Data associated with (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Free Base Hydrate Form 2.

| 2-θ, ° | d-spacing, Å | Relative Intensity, % |
|---|---|---|
| 4.24 | 20.82 | 44 |
| 10.04 | 8.81 | 19 |
| 12.78 | 6.92 | 49 |
| 13.48 | 6.57 | 7 |
| 14.22 | 6.23 | 14 |
| 14.98 | 5.91 | 30 |
| 15.79 | 5.61 | 26 |
| 16.76 | 5.29 | 29 |
| 17.92 | 4.95 | 82 |
| 18.89 | 4.70 | 100 |
| 19.70 | 4.51 | 49 |
| 20.41 | 4.35 | 74 |
| 20.76 | 4.28 | 87 |
| 21.26 | 4.18 | 56 |
| 22.16 | 4.01 | 40 |
| 22.85 | 3.89 | 16 |
| 24.88 | 3.58 | 11 |
| 25.75 | 3.46 | 18 |
| 26.85 | 3.32 | 8 |
| 28.16 | 3.17 | 14 |
| 28.67 | 3.11 | 13 |
| 29.37 | 3.04 | 5 |
| 31.52 | 2.84 | 8 |
| 33.60 | 2.67 | 2 |
| 34.50 | 2.60 | 3 |
| 37.72 | 2.39 | 3 |

HCl Form 1 Powder X-Ray Diffraction Data

Figure 2:
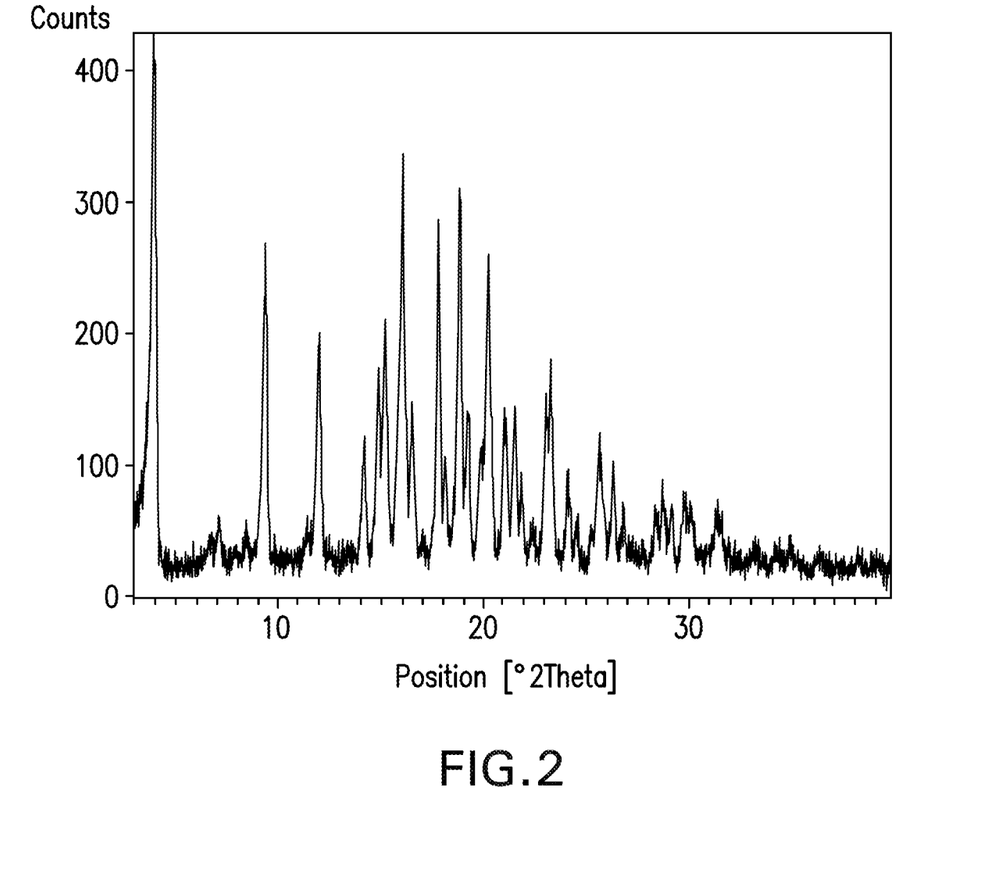
FIG. 2 is graph of Powder X-Ray Diffraction Data associated with (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide HCl Form 1.

| 2-θ, ° | d-spacing, Å | Relative Intensity, % |
|---|---|---|
| 3.99 | 22.14 | 100 |
| 7.08 | 12.49 | 8 |
| 8.44 | 10.48 | 6 |
| 9.39 | 9.42 | 53 |
| 11.95 | 7.41 | 46 |
| 14.14 | 6.26 | 24 |
| 14.80 | 5.99 | 37 |
| 15.17 | 5.84 | 46 |
| 16.00 | 5.54 | 71 |
| 16.51 | 5.37 | 32 |
| 17.78 | 4.99 | 67 |

| 2-θ, ° | d-spacing, Å | Relative Intensity, % |
| --- | --- | --- |
| 18.12 | 4.90 | 20 |
| 18.81 | 4.72 | 75 |
| 19.22 | 4.62 | 31 |
| 20.20 | 4.40 | 61 |
| 21.02 | 4.23 | 29 |
| 21.55 | 4.12 | 30 |
| 21.85 | 4.07 | 17 |
| 22.37 | 3.97 | 8 |
| 23.05 | 3.86 | 32 |
| 23.31 | 3.82 | 34 |
| 24.12 | 3.69 | 16 |
| 25.59 | 3.48 | 21 |
| 26.34 | 3.38 | 18 |
| 26.85 | 3.32 | 12 |
| 28.73 | 3.11 | 15 |
| 29.17 | 3.06 | 12 |
| 29.81 | 3.00 | 13 |
| 30.17 | 2.96 | 11 |
| 31.35 | 2.85 | 10 |
| 33.21 | 2.70 | 4 |
| 34.84 | 2.58 | 3 |
| 36.42 | 2.47 | 2 |

HCl Hydrate Form 1 Powder X-Ray Diffraction Data

Figure 3:
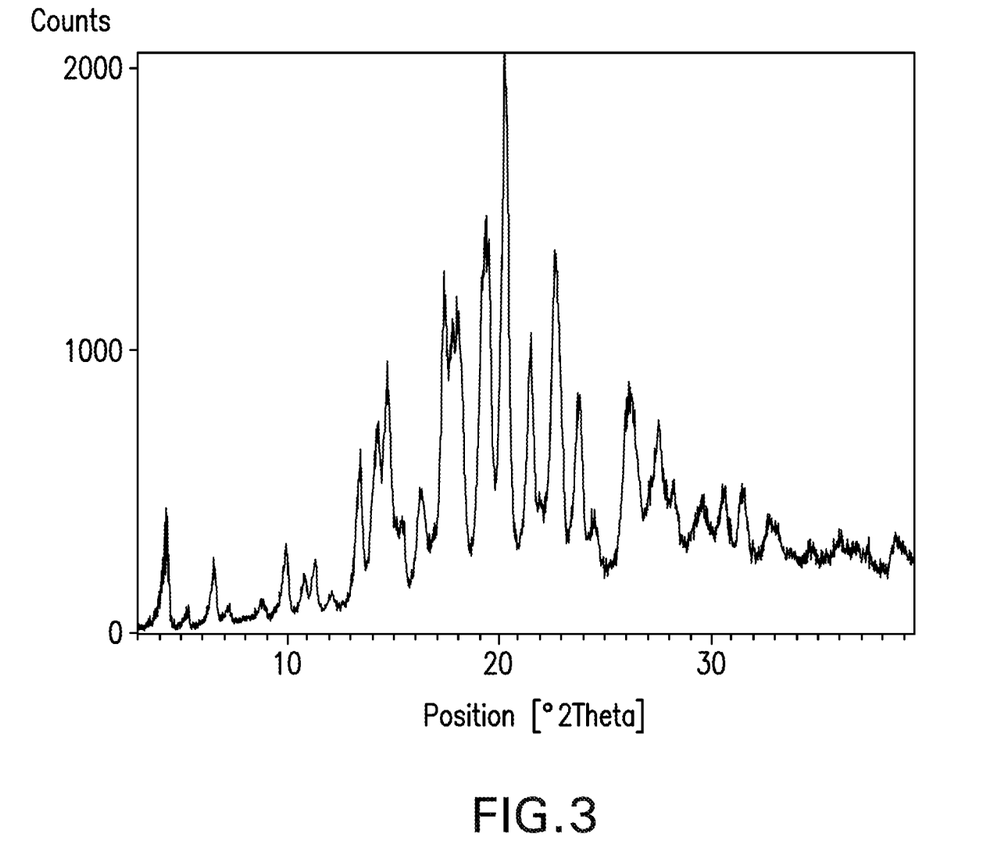
FIG. 3 is graph of Powder X-Ray Diffraction Data associated with (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide HCl Hydrate Form 1.

| 2-θ, ° | d-spacing, Å | Relative Intensity, % |
| --- | --- | --- |
| 4.34 | 20.38 | 16 |
| 5.31 | 16.63 | 2 |
| 6.57 | 13.45 | 9 |
| 7.20 | 12.28 | 3 |
| 8.79 | 10.07 | 3 |
| 9.93 | 8.91 | 11 |
| 10.76 | 8.22 | 7 |
| 11.25 | 7.87 | 9 |
| 12.03 | 7.36 | 3 |
| 13.39 | 6.61 | 25 |
| 14.12 | 6.27 | 32 |
| 14.67 | 6.04 | 41 |
| 15.38 | 5.76 | 14 |
| 16.22 | 5.46 | 21 |
| 17.31 | 5.12 | 59 |
| 18.17 | 4.88 | 43 |
| 19.08 | 4.65 | 54 |
| 19.41 | 4.57 | 67 |
| 20.21 | 4.39 | 100 |
| 21.42 | 4.15 | 45 |
| 22.58 | 3.94 | 63 |
| 23.77 | 3.74 | 33 |
| 24.50 | 3.63 | 12 |
| 26.11 | 3.41 | 35 |
| 27.51 | 3.24 | 28 |
| 28.25 | 3.16 | 15 |
| 29.57 | 3.02 | 13 |
| 30.61 | 2.92 | 14 |
| 31.47 | 2.84 | 14 |
| 32.70 | 2.74 | 7 |
| 38.69 | 2.33 | 5 |

HCl Hydrate Form 2 Powder X-Ray Diffraction Data

Figure 4:
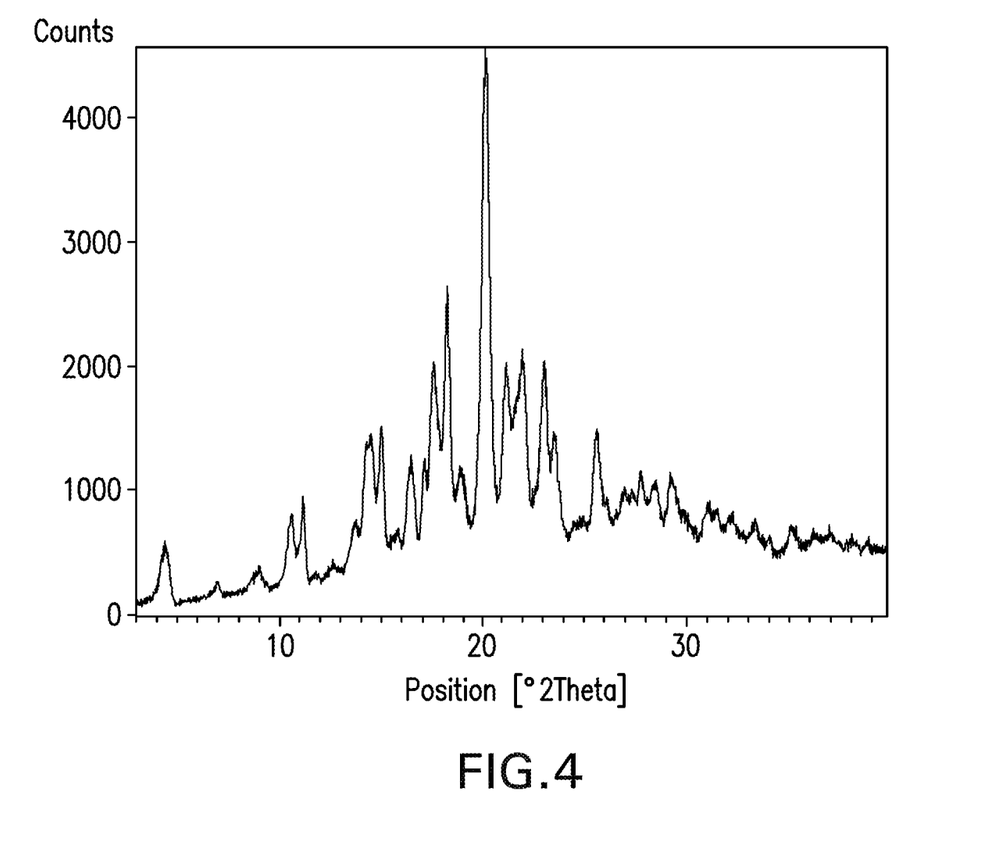
FIG. 4 is graph of Powder X-Ray Diffraction Data associated with (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide HCl Hydrate Form 2.

| 2-θ, ° | d-spacing, Å | Relative Intensity, % |
| --- | --- | --- |
| 4.53 | 19.49 | 15 |
| 7.07 | 12.51 | 3 |
| 9.10 | 9.72 | 5 |
| 10.69 | 8.27 | 15 |
| 11.24 | 7.87 | 18 |
| 13.76 | 6.44 | 12 |
| 14.29 | 6.20 | 27 |
| 14.58 | 6.08 | 28 |
| 15.03 | 5.90 | 30 |
| 16.60 | 5.34 | 22 |
| 17.16 | 5.17 | 23 |
| 17.59 | 5.04 | 42 |
| 18.31 | 4.85 | 58 |
| 18.95 | 4.68 | 21 |
| 20.20 | 4.40 | 100 |
| 21.17 | 4.20 | 41 |
| 22.01 | 4.04 | 42 |
| 23.05 | 3.86 | 41 |
| 23.57 | 3.78 | 27 |
| 25.65 | 3.47 | 27 |
| 26.99 | 3.30 | 14 |
| 27.81 | 3.21 | 18 |
| 28.53 | 3.13 | 15 |
| 29.24 | 3.05 | 16 |
| 31.07 | 2.88 | 9 |
| 32.25 | 2.78 | 8 |
| 33.44 | 2.68 | 6 |
| 35.26 | 2.55 | 4 |
| 36.85 | 2.44 | 2 |

Film Cast Process

Film casting method can be used as preliminary screening technique to determine the right amount of drug-polymer or plasticizer combination that can yield molecularly dispersed drug. Briefly, the drug and the polymer are dissolved in different ratios in a common solvent having adequate drug polymer solubility/mixture of solvents followed by film formation on a glass surface by evaporation of the solvent at 24° C. for 24 hours to remove residual solvent in the film cast that can otherwise affect the stability of the solid dispersion. A volatile solvent is preferred over water or high boiling point solvents as the solvent would take longer time to evaporate and there is a possibility of incomplete drying of the film. The film is subsequently pulverized using a mortar and pestle and sieved to get solid dispersion of appropriate size which is then filled into capsules. The pulverized film is analyzed for its amorphous nature via DSC, XRD and other analytical tools.

Hot Melt Extrusion Process

Solid dispersions of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide can be created using an extrusion process such as a hot melt extrusion process. Briefly, (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide hydrate Form 2 (DS) and a polymer such as hypromellose acetate succinate are blended in a mixer such as a Turbula mixer in a DS:polymer weight ratio between about 1:1 and 1:5 followed by feeding of the powder mixture using a vibration feeder to an extruder such as the Leistritz Nano 16 mm twin screw extruder. The drug polymer blend is extruded and resulting extrudate is quenched in, for example, liquid nitrogen, and subsequently milled using a grinder. The milled extrudate is sieved and blended extragranularly with a superdisntegrant such as crospovidone at 10% w/w of the extrudate for 5 minutes using a mixer such as a Turbula mixer, and the extrudate/disintegrant blend is subsequently used to prepare a pharmaceutical formulation such as a hard gelatin capsule by filling the capsule.

The solid dispersion composition prepared either via a film cast method or hot melt extrusion results in the formation of an amorphous form, which after grinding is filled into the capsules and is the desirable form leading to solubilization enhancement for enhancing drug bioavailability.

Tablets comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous form prepared via film casting or hot melt extrusion can be formed using conventional tableting procedures and vehicles and other excipients including diluents (such as lactose, avicel, mannitol, dibasic calcium phosphate) disintegrants (such as croscarmellose sodium, crospovidone, sodium starch glycollate), salt disintegrants (such as NaCl, NaHCO$_3$, KH$_2$PO$_4$, K$_2$SO$_4$, KCl), binders (such as povidone, hydroxypropyl methylcellulose, hydroxypropyl cellulose), glidants/flow promoters (such as silicon di-oxide), lubricants (magnesium stearate, sodium stearyl fumarate) and anti-oxidants (for example BHT, BHA, propyl gallate) to improve the chemical stability of the formulation.

The absence of the crystalline peaks, as evidenced by XRD analysis, indicated that (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide was amorphous in the solid dispersion formulation. DSC thermogram of the solid dispersion formulation showed a Tg of 110° C. which signifies physical stability. The absence of a melting endotherm at 133° C. (the melting point of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide hydrate Form 2 is 133° C.) also indicated that (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide is amorphous in the solid dispersion formulation.

hypromellose acetate succinate were prepared via solvent casting technique according to the following procedure:

Step 1: (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline hydrate Form 2 (HF-2) and the granular polymer hypromellose acetate succinate grade M was dissolved in acetone in a 1:3 (% w/w) ratio (drug load 25%) followed by evaporation of the solvent followed by vacuum drying of the film cast to further remove any residual solvent.

Step 2: The film casts were crushed/grinded and sieved through a #16 mesh.

The crushed dispersion was subsequently filled into a size 00 hard gelation capsule. 100 mg (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide and 300 mg of hypromellose acetate succinate were loaded into a capsule.

The solid dispersion with hypromellose acetate succinate resulted in significantly enhanced dissolution in a 2-stage dissolution study with a ~10 fold increase in exposure compared to the crystalline HF-2 at ~50 mg dose. Furthermore, DSC data indicated good physical stability of the solid dispersion with a Tg of ~120° C.

Pre-clinical dog pharmacokinetic studies show that solid dispersions prepared via film casting outperform other suspension-based formulations of the (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide hydrate Form 2.

TABLE 1a

Results of pre-clinical dog pharmacokinetic studies of (S)-N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Example 1a (50 mg dose)

| Dose | HF-2 hg suspension 50 mg/kg | | HF-2 suspension 50 mg/kg | | HF-2 np suspension 43.1 mg/kg | | AF HPMCAS Example 1a 44.6 mg/kg | |
|---|---|---|---|---|---|---|---|---|
| | Mean | CV (%) | Mean | CV (%) | Mean | CV (%) | Mean | CV (%) |
| Cmax (ng/mL) | 293 | −75 | 365 | −54 | 1820 | −55 | 2730 | −37 |
| Tmax (hr) | 4 | (1.5-6) | 3 | (2-4) | 3 | (2-6) | 4 | (2-4) |
| AUC (24) ng-hr/mL | 2000 | −77 | 2020 | −74 | 12300 | −78 | 17700 | −39 |
| AUC (I) μM-hr | 2.96 | −78 | 2.95 | −73 | 17.9 | −78 | 25.9 | 39 |
| t½ (hr) | 2.26 | −19 | 2.52 | −30 | 9.03 | −93 | 13.1 | (NC) |

Example 1

Solid dispersions of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Example 1a—Film Cast Process Films of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide solid dispersion with "HF-2" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline hydrate Form 2. "AF" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous form. "HPMCAS" is hypromellose acetate succinate. "hg" is hand ground. "np" is nanoparticle.

Example 1b—Hot Melt Extrusion Process

Hot melt extrusion formulations of (S)—N-(3-(6-isopropoxypyridin-3-yl)-1H-indazol-5-yl)-1-(2-(4-(4-(1- methyl-1H-1,2,4-triazol-3-yl)phenyl)-3,6-dihydropyridin-1(2H)-yl)-2-oxoethyl)-3-(methylthio)pyrrolidine-3-carboxamide (drug) with hypromellose acetate succinate (L and M grades with pH sensitivity of 5.5 and 6.0 respectively) were prepared at 25% drug load using a 16 mm Leistritz twin screw extruder with co-rotating screws using the following process conditions (barrel temp of ~120-130 C); screw speed: ~250 rpm and a 25:1 L/D configuration for the barrel.

(S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline hydrate Form 2. Formulations prepared by hot melt extrusion also resulted in an exposure that was 1.6 fold higher than the amorphous suspension formulation of the drug. The formulation performance of the hot melt extrusion formulations was comparable to the (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline hydrate Form 2 HCL salt of the drug present as a blend/suspension form TABLE 1b Results of pre-clinical dog pharmacokinetic studies of (S)-N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide Example 1b (50 mg dose)

| Dose | AF suspension 50 mg/kg | | HF-2 HCl suspension 50 mg/kg | | HF-2 HCl capsule 50 mg/kg | | AF HPMCAS-L capsule Example 1b 58.8 mg/kg | | AF HPMCAS-M capsule Example 1b 55.5 mg/kg | |
|---|---|---|---|---|---|---|---|---|---|---|
| | Mean | CV (%) | Mean | CV (%) | Mean | CV (%) | Mean | CV (%) | Mean | CV (%) |
| Cmax (ng/mL) | 4602 | (34) | 6490 | (21) | 4523 | (30) | 4367 | (54) | 7056 | (43) |
| Tmax (hr) | 4 | (4-8) | 4 | (4-8) | 8 | (3-12) | 6 | (4-12) | 6 | (4-12) |
| AUC (24) ng-hr/mL | 47687 | (41) | 65750 | (27) | 57008 | (46) | 52244 | (55) | 85232 | (39) |
| AUC (I) μM·hr | 69.3 | | 95.2 | | 86.3 | | 80.5 | | 130 | |
| t½ (hr) | 1.89 | (11) | 2.25 | (37) | 2.62 | NC | 3.71 | (63) | 4.89 | (31) | dine-3-carboxamide crystalline hydrate Form 2 and hypromellose acetate succinate were blended in a Turbula mixer in a ratio of 1:3 (25% drug load) followed by feeding of the powder mixture using a vibration feeder to the Leistritz Nano 16 mm twin screw extruder. The drug polymer blend was extruded using the extrusion conditions as mentioned above. Following extrusion, the extrudate was quenched in liquid nitrogen and subsequently milled using a grinder. The crushed extrudate was passed through a size 30 mesh. The sieved extrudate was blended extragranularly with superdisintegrant crospovidone at 10% w/w of the extrudate for 5 minutes using a Turbula mixer.

The extrudate and disintegrant blend subsequently filled into a size 00 hard gelatin capsule. 100 mg (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide, 300 mg hypromellose acetate succinate and 40 mg crospovidone were loaded into a capsule.

Formulations prepared by extrusion significantly enhanced dissolution of the drug. In a 2-stage dissolution study, M grade was superior to L grade. The DSC analysis of the extrudates indicated good physical stability displaying a Tg of ~110° C. XRD analysis demonstrated lack of crystalline peaks, indicating the drug was amorphous for both the hypromellose acetate succinate M and hypromellose acetate succinate L extrudate. Results of dog PK study of different (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide formulations at 50 mg/kg dose Formulations prepared by hot melt extrusion resulted in an exposure that was 25-40 fold higher than (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline hydrate Form 2.

"HF-2" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide crystalline hydrate Form 2. "AF" is (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous form. "HPMCAS L" is hypromellose acetate succinate grade L. "HPMCAS M" is hypromellose acetate succinate grade M. "CV (%)" is coefficient of variation.

What is claimed is:

1. A process for preparing a composition comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide and hypromellose acetate succinate, wherein said process comprises the steps of:
   a) blending (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide hydrate form 2 and hypromellose acetate succinate to form a blend,
   b) extruding the blend through a twin screw hot melt extruder to form an extrudate,
   c) quenching the extrudate on an air cooled conveyor belt or using a chilled roller to form quenched extrudate comprising (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide amorphous form, and
   d) pelletizing the extrudate to form pellets and subsequently milling the pellets to form a ground product.

2. A The process of claim 1, wherein the weight ratio of (S)—N-(3-(6-isopropoxypyridin-3-yl)-1H-indazol-5-yl)-1-(2-(4-(4-(1-methyl-1H-1,2,4-triazol-3-yl)phenyl)-3,6-dihydropyridin-1(2H)-yl)-2-oxoethyl)-3-(methylthio)pyrrolidine-3-carboxamide to hypromellose acetate succinate is between about 1:1 and 1:5.

3. A The process of claim 2, wherein the ratio is about 1:3.

* * * * *